United States Patent [19]

Hara et al.

[11] Patent Number: 4,632,550
[45] Date of Patent: Dec. 30, 1986

[54] MEASURING METHOD FOR A TIME RESOLVED EMISSION SPECTRUM OR A TIME RESOLVED EXCITATION SPECTRUM

[75] Inventors: Kiyoaki Hara; Issei Yokoyama; Natsuki Yoshida, all of Kyoto, Japan

[73] Assignee: Horiba, Ltd., Kyoto, Japan

[21] Appl. No.: 657,963

[22] Filed: Oct. 5, 1984

[30] Foreign Application Priority Data

Oct. 13, 1983 [JP] Japan .................... 58-191722

[51] Int. Cl.[4] ............................................. G01J 3/443
[52] U.S. Cl. ..................................... 356/311; 356/317
[58] Field of Search .............. 356/301, 311, 313, 317, 356/318; 250/458.1, 459.1, 461.1, 461.2, 365

[56] References Cited

PUBLICATIONS

Wilson et al., *Analytical Chemistry*, vol. 47, No. 2, Feb. 1975, pp. 256–266.
Leskovar et al., *Review of Scientific Instruments*, vol. 47, No. 9, Sep. 1976, pp. 1113–1121.
Lawton et al., *Journal of Physics E: Scientific Instruments* vol. 9, 1976.
Horns et al., *Analytical Chemistry*, vol. 48, No. 13, Nov. 1976, pp. 1937–1943.

*Primary Examiner*—F. L. Evans
*Attorney, Agent, or Firm*—Wenderoth, Lind & Ponack

[57] ABSTRACT

A measuring method for a time resolved emission spectrum or a time resolved excitation spectrum, wherein when emission transient waveforms from a pulse-excited sample are measured by the time correlation photon counting method; the emission transient waveforms are measured at every optimum wavelength in a problematical emission spectrum region; the measured emission transient waveforms are stored in a memory in order and at every wavelength; all the transient waveforms in each wavelength are measured; thereafter, the time resolved emission spectrum or the time resolved excitation spectrum is produced on the basis of all the above-mentioned stored emission transient waveform data, thereby enabling the proper spectrum to be produced efficiently.

3 Claims, 4 Drawing Figures

MEASURING METHOD FOR A TIME RESOLVED EMISSION SPECTRUM OR A TIME RESOLVED EXCITATION SPECTRUM

BACKGROUND OF THE INVENTION

1. Field of the Invention

This invention relates to a measuring method for measuring the light emission from a pulse-excited sample so as to obtain a time resolved emission spectrum or a time resolved excitation spectrum. The time resolved emission spectrum is given by the three-dimensional curve including the time axis of the emission spectrum with the time t as the X-axis, wavelength λ as the Y-axis, and emission intensity as the Z-axis. The spectrum represented two-dimensionally, is the emission spectrum at the cut face of the three-dimensional curve when cut by a plane perpendicular to the X-axis; in brief, the time resolved emission spectrum is the characteristic curve of wavelength-to-emission intensity at a certain time. The time resolved excitation spectrum is the characteristic curve of excitation wavelength dependency for the emission intensity.

2. Description of the Prior Art

The conventional measuring method for the time resolved emission spectrum or the time resolved excitation spectrum, is basically a certain sampling measurement which uses the time correlation photon counting method using a time-to-amplitude converter (to be hereinafter called a TAC), and has the highest sensitivity and accuracy. FIG. 1 illustrates an apparatus used to measure the time resolved emission spectrum. In FIG. 1, element 1 is a TAC and element 2 is a sample; element 3 is a pulse light source for pulse-exciting the sample 2; 4 is a spectroscope; element 5 is a detector, for example, photomultiplier, for detecting only the wavelength selected by the spectroscope 4 from among the light emission wavelengths from the sample 2; element 6 is a photomultiplier for detecting the light emission from the pulse light source 3; elements 7 and 8 are pulse shaper circuits; element 9 is a single channel pulse height and analyzer; element 10 is a multichannel scaler; element 11 is a stepping motor drive unit for adjusting the wavelength of spectroscope 4; element 12 is a clock pulse generator; element F is a filter and L is a lens.

The TAC 1 uses, as the start pulse, the detection signal from the photomultiplier 6 which detects the light from the pulse light source 3 and uses, as the stop pulse, the detection signal from the photomultiplier 5 which detects the light emission from the sample 2. Accordingly, an output of the TAC 1 develops a voltage proportional to the time from the start pulse to the stop pulse (to be hereinafter called the reference time). The voltage is fed to the single channel pulse height analyzer 9 (to be hereinafter called an SCA). The SCA 9 is a linear logic converter having two pulse height discriminators capable of separately setting the pulse height discrimination level so that a logic output pulse is generated only when the pulse height of linear input pulses exists between upper and lower limit levels. In other words, the voltage crest values at the upper and lower limits of the SCA are properly adjusted, whereby the signal developed in a certain time region (the time window) of the TAC 1 is the logic output pulse of the SCA 9. Hence, the wavelength of spectroscope 4 is adjusted in the direction of fixing the time region. The aforesaid measurement is carried out at every optimum wavelength, and the output of the SCA 9 is input into channels corresponding to the respective wavelengths of multichannel scaler 10, thereby making it possible to obtain the time resolved emission spectrum in a certain time region of emission transient waveforms corresponding to the voltage window fixed by the SCA 9. Next, the time window of the TAC 1, as set by the SCA 9, is changed by a proper amount from the former time window and the spectroscope 4 is rescanned, thereby obtaining the time resolved emission spectrum at the different time regions, such operation being carried out by changing various time windows to repeat the same measurements as the above.

The above conventional method, however, has the following defects:

①  The spectroscope is scanned once to obtain only the emission spectrum at the time window of width Δt delayed by a predetermined time ti from the reference time, so that the information occurring at a time other than during the time window, in spite of being measured by the TAC 1, is not taken as the SCA 9 output and not used as data. Therefore, it takes a long time to obtain the time resolved emission spectrum because the time window should be shifted to various positions and the spectroscope should be scanned several times to repeat the measurement. ② In order to obtain the proper time resolved emission spectrum, the time region set by the time window decided by the initial and last time windows, the width of the time window, the intervals between the time windows, and the number of windows, should be properly selected, which is not determinable unless trial-and-error measurements are repeated several times, thereby requiring a great deal of time and labor.

The defects noted in the items ① and ② are involved in the measuring method for the time resolved excitation spectrum and the time resolved emission spectrum, because when the spectroscope 4 is disposed for the first time between the specimen 2 and the light source 3, the time resolved excitation spectrum is measurable in the same fashion as the time resolve emission spectrum.

SUMMARY OF THE INVENTION

As object of the invention is to provide a novel measuring method which thoroughly eliminates the aforesaid defects in the conventional method and finishes the measurement by scanning once the spectroscope at a wavelength, thereby obtaining the necessary and proper time resolved emission spectrum or time resolved excitation spectrum.

The measuring method for the time resolved emission spectrum or time resolved excitation spectrum of the invention is summarized in that when the emission transient waveform from the pulse-excited sample is measured by a time correlation photon counting method, the emission transient waveform is measured at every wavelength in the problematical emission spectrum region; the emission transient waveforms are stored in a memory means in order and at every wavelength; the transient waveforms of the respective wavelengths end prior to a complete measurement, and thereafter the time resolved emission spectrum or time resolved excitation spectrum is produced on the basis of data of all of the emission transient waveforms.

The above and further objects and novel features of the invention will more fully appear from the following detailed description in accordance with the accompanying drawings.

DESCRIPTION OF THE PREFERRED EMBODIMENT

Figure 1:
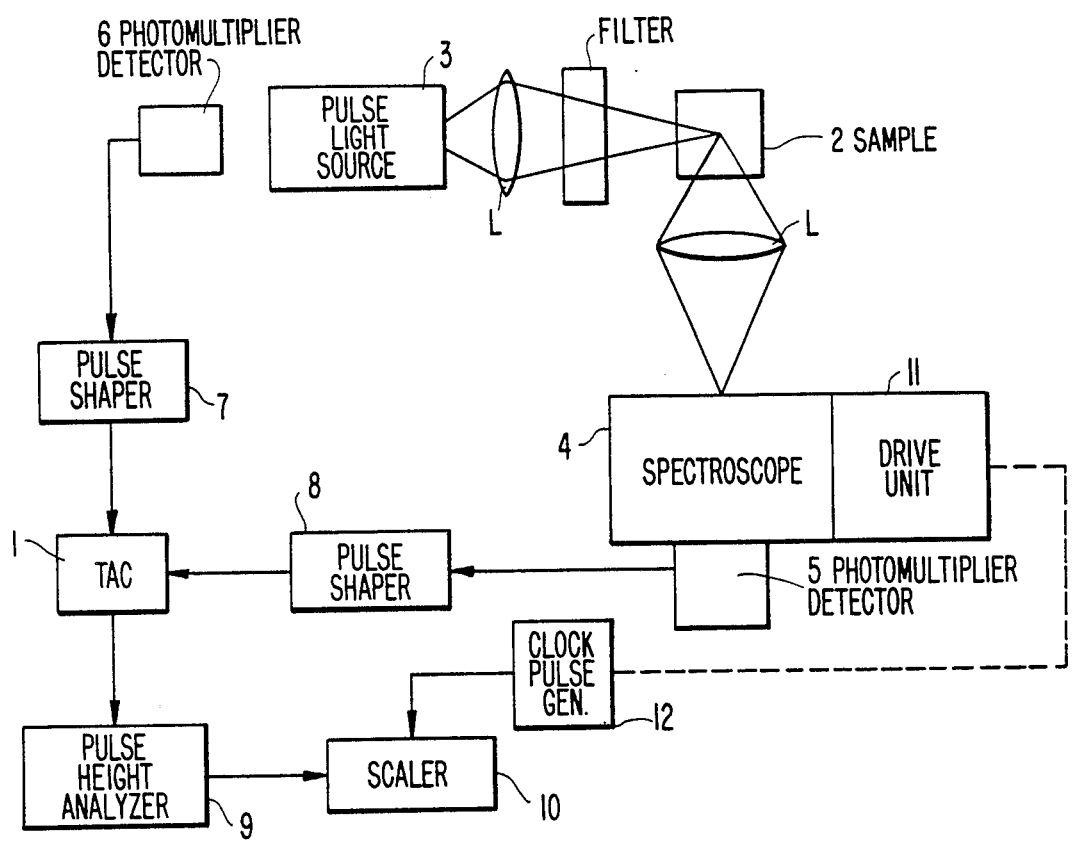
FIG. 1 is a block diagram of an apparatus for a conventional measuring method.
Figure 2:
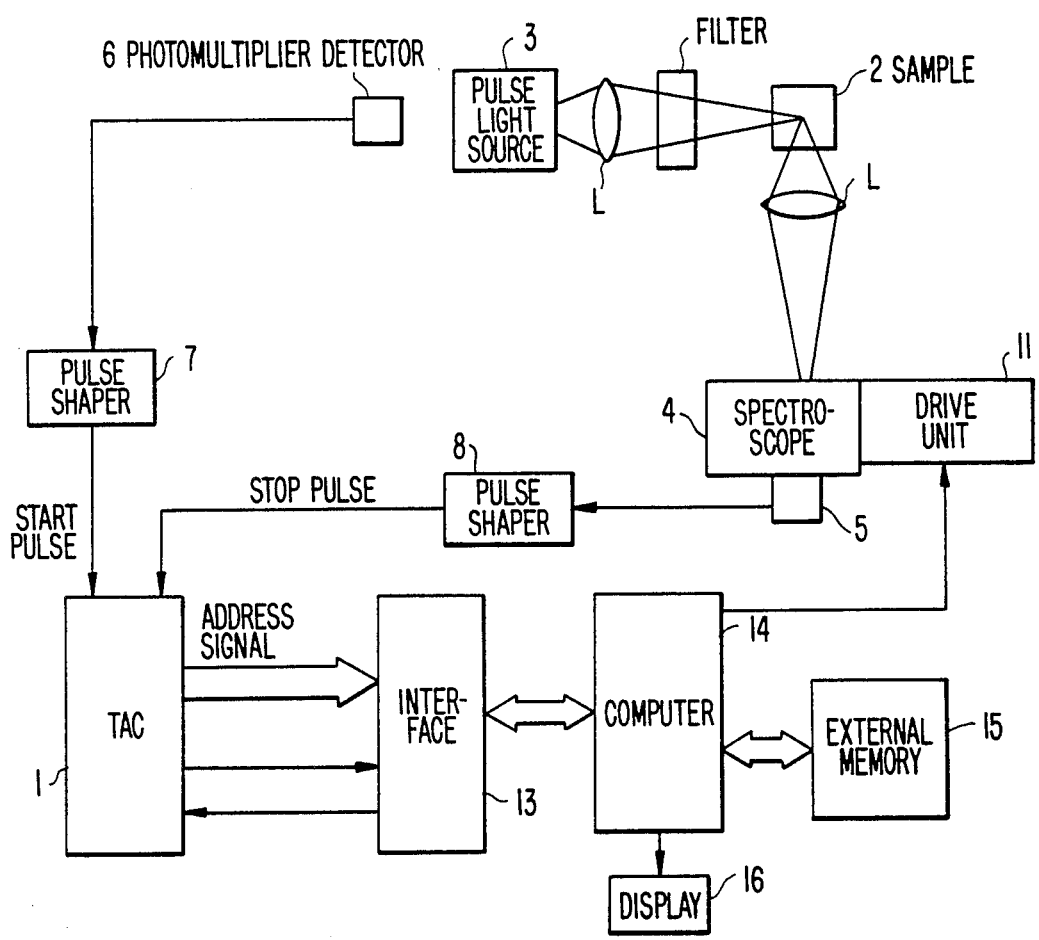
FIG. 2 is a block diagram of an apparatus for carrying out a measuring method in accordance with the present invention for the time resolved emission spectrum.

FIG. 2 is a view exemplary of an apparatus for carrying out the measuring method for a time resolved emission spectrum of the invention in which the same components as those in FIG. 1 are designated by the same reference numerals. In FIG. 2, reference numeral 13 designates a TAC interface; element 14 is a computer; element 15 is an external memory for the computer 14 (for example, a floppy disk unit), and element 16 is a device to display the result of the data processing by the computer, e.g. a CRT.

The TAC 1, which is the same as that of the conventional apparatus in FIG. 1, uses the detection signal from photomultiplier 6 as the start pulse and the signal from photomultiplier 5 as the stop pulse, thereby generating a voltage proportional to the time between the start pulse and the stop pulse. The apparatus, however, is different from the conventional apparatus in FIG. 1 in that the time-to-amplitude conversion value of TAC 1 is stored in the external memory 15 of the computer 14 in the wavelength set of the generation frequency distribution (histogram) by adding a logical 1 to the corresponding address as the address signal after the end of a measurement. Hence, when the number of excitation pulses or the measurement time decides the measurement end condition, the emission transient waveform in one wavelength $\lambda_1$ selected by the spectroscope 4 is stored in the external memory 15, where the emission transient waveform corresponds to the characteristic curve on the cut face when cut by the plane perpendicular to the Y-axis and is the so-called histogram representing the time on the axis of abscissa and the emission intensity on the axis of ordinate.

Figure 4:
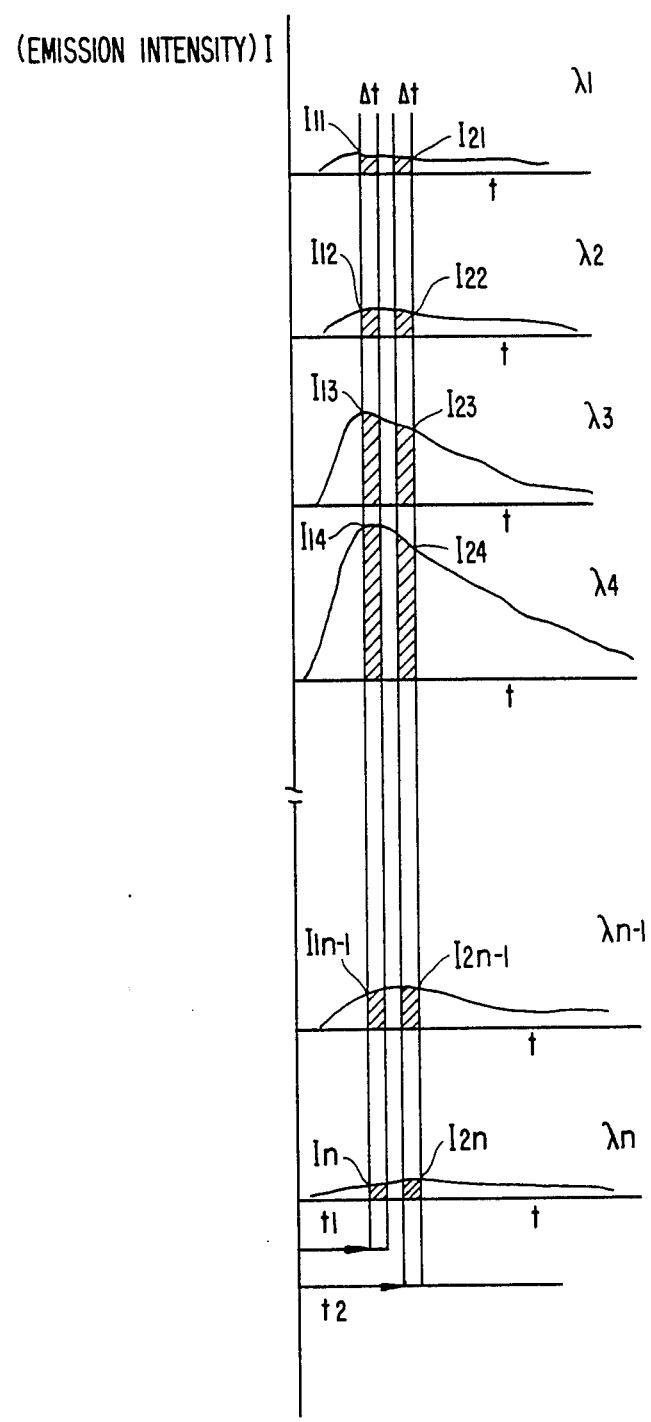
FIG. 4 is a waveform chart showing the emission transient characteristic at every wavelength.

Thus, upon obtaining the emission transient waveform in one wavelength $\lambda_1$, the stepping motor 11 is driven to scan the wavelength of spectroscope 4 and the same measurement is again carried out at a different wavelength $\lambda_2$ so as to thereby obtain the emission transient waveform, which is carried out at optimum wavelengths $\lambda_1$ to $\lambda_n$. Upon finishing the measurement for all of the problematical wavelengths, the external memory 15 has stored therein the emission transient waveforms at the respective wavelengths $\lambda_1$ to $\lambda_n$ as shown in FIG. 4. Hence, the computer 14 reads out the emission intensity $I_{11}$, $I_{12}$, $I_{13}$ . . . during the time $\Delta t$ for the time $t_1$ from all of the emission transient waveforms within the external memory 15, whereby the time resolved emission spectrum for the time $t_1$ from the reference time is obtainable. Similarly, when the emission intensity $I_{21}$, $I_{22}$, $I_{23}$ . . . at the time $t_2$ are read out, the time resolved emission spectrum for the time $t_2$ from the reference time is obtainable. In this case, when the channel (time) of the initial time window, the width $\Delta t$ of time window, the interval between the time windows, and the number of time windows, are assigned as the input conditions to the computer 14, then the time resolved emission spectrum in the desired time width for the desired time $t_1$ to $t_n$ can be produced.

Figure 3:
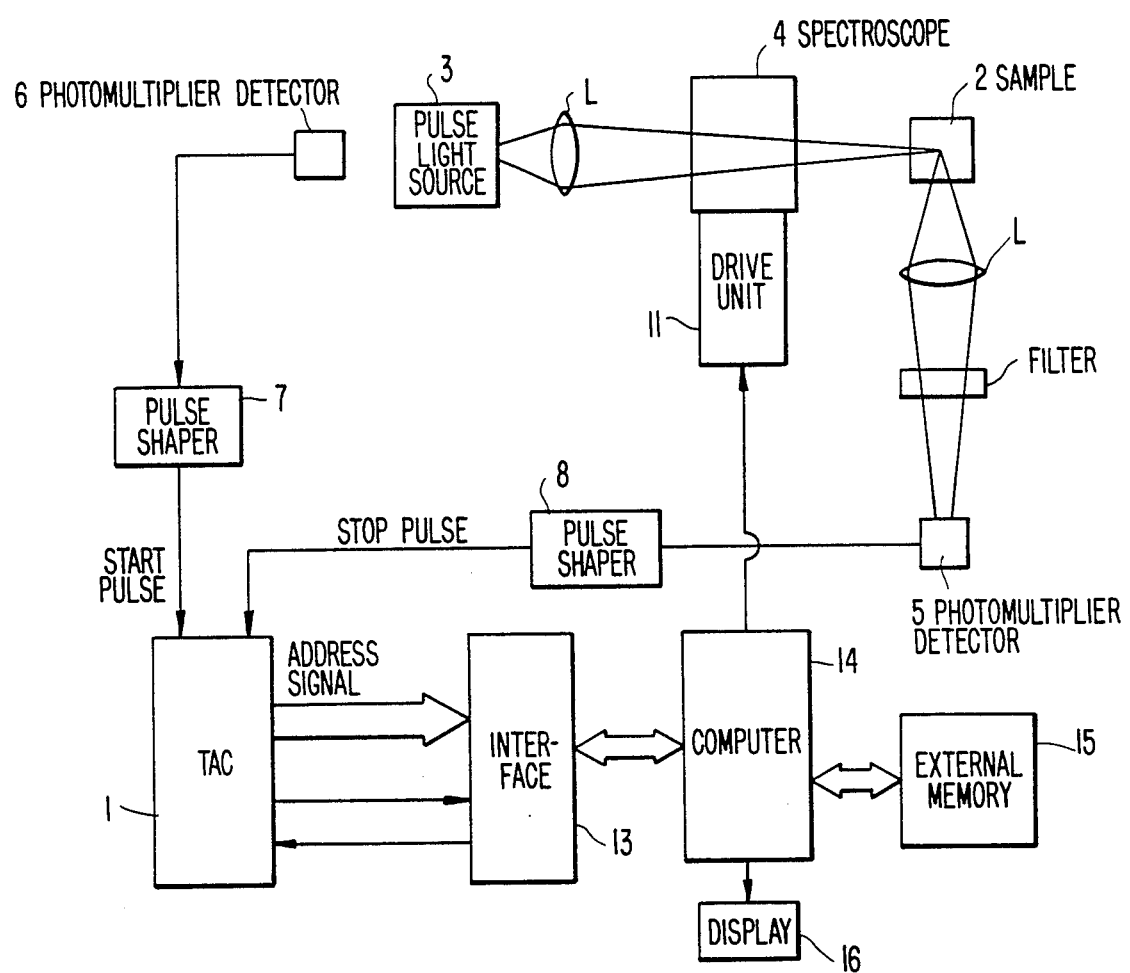
FIG. 3 is a block diagram of an apparatus for carrying out the measuring method in accordance with the present invention for the time resolved excitation spectrum.

FIG. 3 is a view exemplary of an apparatus used for measuring the time resolved excitation spectrum which uses the same principle as the aforesaid embodiment of the invention, but which is only different from FIG. 2 in the location of the spectroscope 4 and identical with respect to the other components, the spectroscope 4 being provided not between the sample 2 and the photomultiplier 5 but between the sample 2 and the light source 3. Such a construction is used to perform a similar measurement so as to thereby obtain the time resolved excitation spectrum.

The measuring method of the present invention for obtaining the time resolved emission spectrum or time resolved excitation spectrum is carried out as noted above so as to be advantageous in the following points:

① The conventional method measures only the information in the time region fixed by the single channel pulse height analyzer and throws out the information in other regions, but the measuring method of the present invention, which keeps all of the information and stores it in the memory means, will eliminate waste in measurement.

② Since the conventional method obtains by measurement at a time one spectrum on the plane perpendicular to the X-axis at the three-dimensional spectrum, the spectroscope scanning must be repeated several times. On the contrary, the measuring method of the present invention, which obtains the emission transient waveform at every wavelength, only once scans the spectroscope so as to obtain the needed information for producing the time resolved emission spectrum and time resolved excitation spectrum, thereby having a superior measuring efficiency and enabling a large reduction in the measuring time.

③ Since the memory means stores the emission transient waveforms in all the problematical wavelengths obtained by scanning the wavelength of the spectroscope, even though the emission transient waveforms thereafter are not at all measured, the data processing by the computer assigns only the initial time window channel, the width of time window, the interval between the time windows and the number of time windows, whereby the time resolved emission spectrum and time resolved excitation spectrum are producible. Hence, the labor and time necessary for producing the proper time resolved emission spectrum and time resolved excitation spectrum are largely saved in comparison with the conventional method.

While a preferred embodiment of the invention has been described using specific terms, such description is for illustrative purpose only, and it is to be understood that changes and variations may be made without departing from the spirit or scope of the following claims.

We claim:

1. A measuring method for a time resolved emission spectrum or a time resolved excitation spectrum, wherein, when emission transient waveforms from a pulse-excited sample are measured by a time correlation photon counting method, said emission transient waveforms are measured at every optimum wavelength in a problematical emission spectrum region, and said measured emission transient waveforms are stored in a memory means in order and at every wavelength, and after all of said transient waveforms at said respective wavelengths are measured, said time resolved emission spectrum or said time resolved excitation spectrum is produced on the basis of all of said stored emission transient waveform data.

2. A measuring method according to claim 1, wherein when said time resolved emission spectrum is measured, a spectroscope is provided between said sample and a light-emission detector.

3. A measuring method according to claim 1, wherein when said time resolved excitation spectrum is measured, a spectroscope is provided between said sample and a light source.

* * * * *